United States Patent [19]

Nobbio

[11] Patent Number: Plant 6,161

[45] Date of Patent: Apr. 26, 1988

[54] CARNATION NAMED BIANCOCHINERA

[76] Inventor: Giacomo Nobbio, Strada Villetta 5, San Remo, Imperia, Italy

[21] Appl. No.: 841,881

[22] Filed: Mar. 20, 1986

[51] Int. Cl. ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler; W. Dennis Drehkoff

[57] ABSTRACT

A new and distinct carnation cultivar characterized by its profuse production of generally white flowers having deeply indented margins. The petals exhibits a slightly yellow coloration at the level of the claw of the petals, and their margins are deeply indented.

1 Drawing Sheet

BACKGROUND OF THE NEW PLANT

This new carnation plant was isolated by spontaneous mutation of the Chinera variety and developed during the course of breeding effort carried on by me at San Remo, Italy. The new plant developed from my crossing of selected varieties of prime breeding stock maintained in my greenhouse in San Remo, Italy, and was discovered in 1981 to possess the generally white flower, sturdiness, and cut flower characteristics that I was seeking.

Asexual propagation of this new plant, by means of cuttings, has been carried out at San Remo, Italy, by me and under my direction through successive generations, and the distinctive characteristics of this plant have been found to hold true from generation to generation and appear to be firmly fixed.

DESCRIPTION OF THE DRAWING

My new variety of carnations is illustrated by the accompanying full color photograhic drawing, which shows a group of flowering stems having buds in various stages of opening, nearly opened flowers and blooms in further stages of maturity. The flower coloration being shown is nearly true as it is reasonably possible to obtain by means of conventional photographic procedures.

DESCRIPTION OF THE NEW PLANT

The following is a detailed description of my new carnation variety, based upon observation of the plants grown under conventional greenhouse practices, with color designations according to The R.H.S. Colour Chart published by The Royal Horticultural Society of London, England.

THE PLANT

Origin: Sport
Parentage:
- *Seed parent.*—Unknown.
- *Pollen parent.*—Unknown.

Classification:
- *Botanic.*—Dyanthus caryophyllus.
- *Commercial.*—Greenhouse carnation for cut flowers.

Form: Bush.
Height: 85–95 cm.
Growth: Vigorous and upright.
Branching: Normal.

Foliage:
- *Quantity.*—Normal.
- *Leaf size.*—Long.
- *Leaf shape.*—Normal.
- *Margin type.*—Entire.
- *Texture.*—Smooth.
- *Color.*—Upper side — dark green; Under side — dark green.

THE BUD

Size: Normal, about 3 cm in diameter and 2.5–3 cm long.
Form: Ovoid-shaped.
Opening rate: Medium.
Color: Green.
Calyx:
- *Size.*—Medium.
- *Shape.*—Funnel-shaped.
- *Aspect.*—Smooth.
- *Splitting.*—The calyx does not split very often.

Sepals:
- *Condition.*—Upstanding.
- *Color.*—Green.

Peduncle: Short and erect.

THE FLOWER

Blooming habits: Continuous and profuse.
Size of bloom: Very large.
- *Diameter.*—When completey open, from 8–11 cm.
- *Depth.*—About 3 cm.

Borne: Singly.
Shape: Flattened cupule in full bloom.
Petalage:
- *Number of petals.*—Over 80.
- *Arrangement.*—Generally imbricated.
- *Form.*—Laciniate.
- *Color.*—The basic color of the petal, at the level of the claw is faint yellow. Generally, however, the petals are white in color, R.H.S. 155/D. The color of the underside of the petal is the same as the upper surface.

Peduncle:
- *Length.*—Short.
- *Color.*—Green.
- *Persistence.*—The flowers hang on and dry.
- *Fragrance.*—Faint.
- *Lasting quality.*—On the plant, good; as a cut flower, good.

REPRODUCTIVE ORGANS

Stamens:

*Number.*—1 to 2, not in every flower and only in the summer.

Anthers:

*Size.*—Normal.

*Color.*—Cream.

Filaments:

*Length.*—1–1.5 cm.

*Color.*—White.

Pollen:

*Color.*—White.

Pistils:

*Number.*—7–8.

Styles:

*Color.*—Cream.

Stigmas:

*Color.*—Cream.

Ovaries:

*Texture.*—Ribbed.

Fruit: Does not set fruit, appears to be sterile.

This new variety of carnation plant is particularly distinguished by the faint yellow color of the claw and white color of the petals. The margin of the petals is deeply indented, with indentations reaching up to 13 mm in depth. The flower is borne on a relatively long, strong peduncle. The flower has a closed calyx which does not split, and the plant has an excellent capacity for continuous and profuse production of blooms which is essential for the cut flower market.

I claim:

1. A new and distinct variety of carnation plant substantially as herein shown and described, characterized by its profuse production of generally white flowers, the flowers being characterized by having a faint yellow coloration at the level of the claw of the petals and a deeply indented margin.

* * * * *

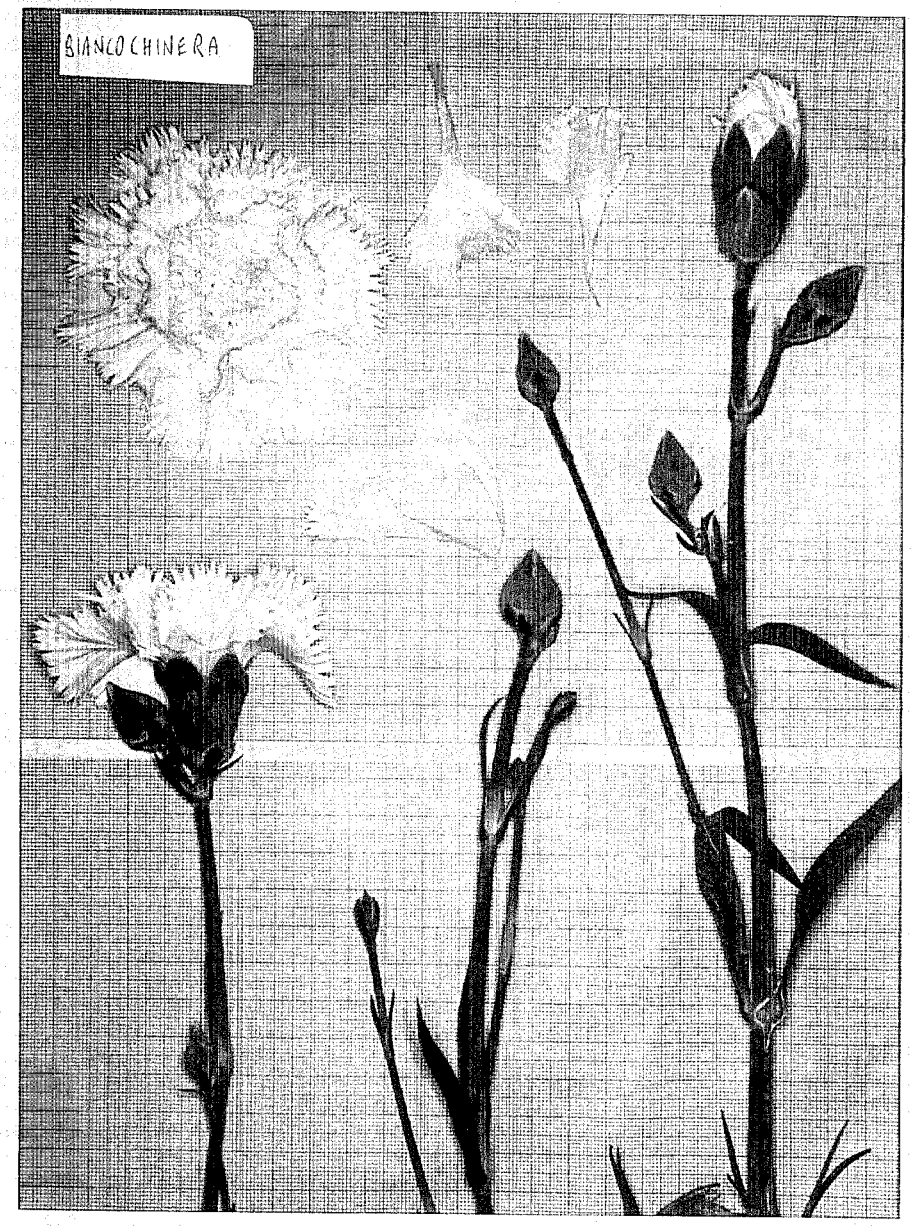
BIANCO CHINERA